(12) United States Patent
DiFoggio

(10) Patent No.: US 12,130,275 B2
(45) Date of Patent: Oct. 29, 2024

(54) CATALUMINESCENCE FOR DOWNHOLE FLUID ANALYSIS

(71) Applicant: Baker Hughes Oilfield Operations LLC, Houston, TX (US)

(72) Inventor: Rocco DiFoggio, Houston, TX (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 251 days.

(21) Appl. No.: 17/891,699

(22) Filed: Aug. 19, 2022

(65) Prior Publication Data

US 2022/0404331 A1 Dec. 22, 2022

Related U.S. Application Data

(62) Division of application No. 16/237,211, filed on Dec. 31, 2018, now Pat. No. 11,573,220.

(51) Int. Cl.
 *G01N 33/28* (2006.01)
 *G01N 21/76* (2006.01)
 *G01V 8/02* (2006.01)

(52) U.S. Cl.
 CPC .......... *G01N 33/2823* (2013.01); *G01N 21/76* (2013.01); *G01V 8/02* (2013.01)

(58) Field of Classification Search
 CPC ....... G01N 33/2823; G01V 8/02; G01V 21/76
 See application file for complete search history.

(56) References Cited

U.S. PATENT DOCUMENTS

| 7,219,541 | B2 | 5/2007 | DiFoggio |
| 7,511,819 | B2 | 3/2009 | DiFoggio |
| 7,553,458 | B2 | 6/2009 | Fleischer |
| 8,145,429 | B2 | 3/2012 | DiFoggio |
| 8,955,375 | B2 | 2/2015 | DiFoggio |
| 9,086,370 | B2 | 7/2015 | Fan |
| 9,234,835 | B2 | 1/2016 | Pelletier |
| 9,850,750 | B1 | 12/2017 | DiFoggio |

(Continued)

FOREIGN PATENT DOCUMENTS

| CN | 101793833 | 8/2010 |
| CN | 101793835 | 8/2010 |

(Continued)

OTHER PUBLICATIONS

Yixin Chu et al., "Highly sensitive dimethyl ether gas sensor utilizing cataluminescence on nanosized MgO/In2O3," 2014, Measurement Science and Technlogy, vol. 25, pp. 1-7.

(Continued)

*Primary Examiner* — John Fitzgerald
(74) *Attorney, Agent, or Firm* — Hogan Lovells US LLP

(57) ABSTRACT

A system for performing a downhole optical analysis includes a housing positioned in a wellbore extending into a formation. The system also includes a carrier arranged within the housing, the carrier being coupled to a power supply. The system further includes a catalyst coating at least a portion of the carrier. The system also includes a regulated inlet providing a fluid pathway into a reaction chamber that includes at least a portion of the catalyst. The system further includes a detector arranged relative to the reaction chamber to detect a signal emitted via an interaction between the catalyst and a fluid sample introduced into the housing.

5 Claims, 5 Drawing Sheets

(56) References Cited

U.S. PATENT DOCUMENTS

| | | | |
|---|---|---|---|
| 11,573,220 B2* | 2/2023 | DiFoggio | ............... G01V 8/02 |
| 2002/0131898 A1 | 9/2002 | Fleischer | |
| 2002/0139528 A1 | 10/2002 | Surjaatmadja | |
| 2009/0200016 A1 | 8/2009 | Goodwin | |
| 2010/0276581 A1 | 11/2010 | Bliven | |
| 2011/0023594 A1 | 2/2011 | Pelletier | |
| 2013/0014940 A1 | 1/2013 | Fripp | |
| 2013/0216460 A1 | 8/2013 | Ayasse | |
| 2015/0004714 A1 | 1/2015 | Hanby | |
| 2016/0201458 A1 | 7/2016 | Hanby | |
| 2017/0362926 A1 | 12/2017 | DiFoggio | |
| 2018/0100391 A1 | 4/2018 | DiFoggio | |

FOREIGN PATENT DOCUMENTS

| | | | |
|---|---|---|---|
| CN | 102393390 B | 6/2013 | |
| CN | 102181286 B | 11/2013 | |
| CN | 104122364 B | 1/2016 | |
| CN | 107021730 A | 8/2017 | |
| CN | 105628856 B | 10/2017 | |
| CN | 108181301 | 6/2018 | |
| CN | 108195826 | 6/2018 | |
| CN | 109187512 | 1/2019 | |
| GB | 2573118 A * | 10/2019 | ............ G01N 21/76 |

OTHER PUBLICATIONS

L. Zhang et al., "Advances in nanomaterial-assisted cataluminescence and its sensing applications," 2015, Trends in Analytical Chemistry, vol. 67, pp. 107-127.

J. Liu et al., "Catalysis-Based Cataluminescent and Conductometric Gas Sensors: Sensing Nanomaterials, Mechanism, Applications and Perspectives," 2016, Catalysts, vol. 210, 23 pages.

K. Zhou et al., "Simultaneous determination of formaldehyde and hydrogen sulfide in air using the cataluminescence of hanosized $Zn_3SnLa_2O_8$," 2016, Microchim. Acta., vol. 183, pp. 1063-1068.

R. Kaushik et al., "Recent progress in hydrogen sulphide (H2S) sensors by metal displacement approach," 2017, Coordination Chemistry Review, vol. 347, pp. 141-157.

X. Dong et al., "MOFs-derived dodecahedra porous $Co_3O_4$: An efficient cataluminescence sensing material for H2S," 2018, Sensors and Actuators B, vol. 258, pp. 349-357.

International Search Report and Written Opinion dated Apr. 8, 2020, corresponding to Application No. PCT/19/65192.

Final Office Action issued in U.S. Appl. No. 16/237,211, dated Dec. 18, 2020.

Non-Final Office Action issued in U.S. Appl. No. 16/237,211, dated Sep. 10, 2020.

Notice of Allowance issued in U.S. Appl. No. 16/237,211, dated Oct. 5, 2022.

Restriction Requirement issued in U.S. Appl. No. 16/237,211, dated Jul. 7, 2020.

* cited by examiner

CATALUMINESCENCE FOR DOWNHOLE FLUID ANALYSIS

CROSS-REFERENCE TO RELATED APPLICATIONS

This is a divisional application of and claims the benefit of co-pending U.S. patent application Ser. No. 16/237,211, titled "CATALUMINESCENCE FOR DOWNHOLE FLUID ANALYSIS," filed Dec. 31, 2018, the full disclosure of which is hereby incorporated by reference in its entirety for all purposes.

BACKGROUND

1. Field of the Invention

The present disclosure relates to downhole measurement systems. More specifically, this application relates to downhole fluid analysis using cataluminescence.

2. Description of Related Art

It is important for oil and gas companies to know the chemical composition and physical properties of fluids in their reservoirs as soon as possible after drilling for improved reservoir evaluation and management and, later, to support flow assurance during well production. Years ago, oil companies did production tests of formation fluids through the drill string and produced many barrels of oil to the surface over a day or two, which was very costly (around $10 million) and also posed safety and environmental risks.

In recent years, downhole formation fluid sampling has largely replaced production testing to retrieve small samples (liters) of fluids to the surface in pressurized tanks for subsequent analysis in a surface lab, which often takes months after sample collection. Of course, the delay in fluid analysis also delays planning for suitable production facilities. Furthermore, trace amounts of important chemicals, such as hydrogen sulfide, which can be important at the 10 ppm level, are often lost to chemical reactions with the tank walls over time leading to erroneously low surface lab measurements of hydrogen sulfide and overly optimistic estimates of the market value of the crude oil and of the cost of tubulars and other facilities to handle the oil without corroding.

More recently, downhole fluid analysis has become more sophisticated and provides real-time chemical composition for many constituents of crude oil or brine such as carbon number distribution (methane, ethane, etc.), or carbon dioxide content, often by infrared spectroscopy, while doing formation testing and sampling. However, trace constituents can be difficult to quantify by infrared. Real-time downhole quantification of hydrogen sulfide in crude oil is currently regarded as questionable by many oil companies.

SUMMARY

Applicant recognized the problems noted above herein and conceived and developed embodiments of systems and methods, according to the present disclosure, for determination of downhole formation properties.

In an embodiment, a method for performing downhole optical fluid analysis includes positioning an optical analysis tool in a downhole environment. The method also includes regulating a flow of a fluid sample into a reaction chamber of the optical analysis tool. The method further includes providing a catalyst within the reaction chamber that reacts with an analyte in the fluid sample to emit light. The method includes detecting the emitted light.

In an embodiment, a method for performing downhole optical fluid analysis includes positioning an optical analysis tool in a downhole environment on a tool string, the optical analysis tool comprising a reaction chamber containing oxygen. The method also includes injecting a predetermined amount of a fluid sample, withdrawn from a downhole formation, into the reaction chamber. The method further includes detecting a first signal when the catalyst is at a first temperature. The method also includes heating a catalyst within the reaction chamber. The method includes detecting a second signal when the catalyst is at a second temperature, the second temperature being greater than the first temperature. The method also includes determining an analyte within the fluid sample, based at least in part on a difference between the first signal and the second signal.

In an embodiment, a system for performing a downhole optical analysis includes a housing positioned in a wellbore extending into a formation. The system also includes a carrier arranged within the housing, the carrier being coupled to a power supply. The system further includes a catalyst coating at least a portion of the carrier. The system also includes a regulated inlet providing a fluid pathway into a reaction chamber that includes at least a portion of the catalyst. The system further includes a detector arranged relative to the reaction chamber to detect a signal emitted via an interaction between the catalyst and a fluid sample introduced into the housing.

BRIEF DESCRIPTION OF DRAWINGS

The present technology will be better understood on reading the following detailed description of non-limiting embodiments thereof, and on examining the accompanying drawings, in which.

DETAILED DESCRIPTION

Figure 1:
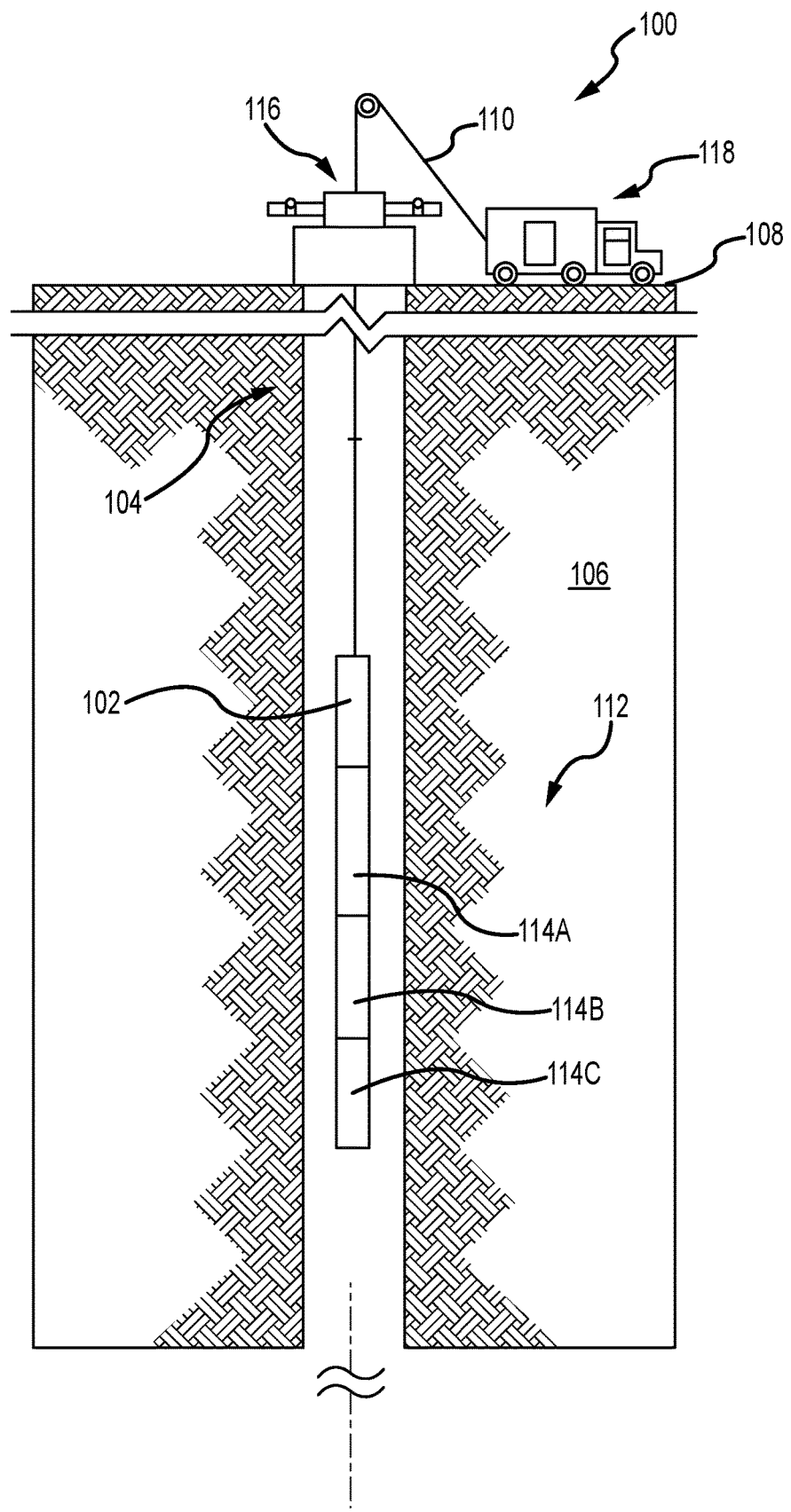
FIG. 1 is a schematic side view of an embodiment of a wireline system, in accordance with embodiments of the present disclosure.

The foregoing aspects, features, and advantages of the present disclosure will be further appreciated when considered with reference to the following description of embodiments and accompanying drawings. In describing the embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "an embodiment", "certain embodiments", or "other embodiments" of the present disclosure are not intended to be interpreted as excluding the existence of additional embodiments that also incorporate the recited features. Furthermore, reference to terms such as "above", "below", "upper", "lower", "side", "front", "back", or other terms regarding orientation or direction are made with reference to the illustrated embodiments and are not intended to be limiting or exclude other orientations or directions.

Chemiluminescence (CL) refers to a chemical reaction that emits light (usually visible light) such as the light of fireflies or the light of breakable-seal glow sticks. Cataluminescence (CTL) is a technique that uses a catalyst, which is not consumed in the reaction, to accelerate chemiluminescence reactions. Cataluminescence, as used in embodiments of the present disclosure, provides an alternative to infrared analysis or to a downhole gas chromatograph to determine the concentrations of analytes such as $H_2S$, methane, ethane, propane, butane, $CO_2$, and the like in natural gas or in crude oil. CTL provides several advantages for use in downhole fluid analysis, including: 1) being highly specific to one chemical, but not to similar chemicals; 2) having high sensitivity to low concentrations of chemicals; 3) having increasing signal (light) intensity with increasing temperatures (due to an increased chemical reaction rate) up to approximately 200 degrees to 300 degrees Celsius, which is above most wellbore temperatures; 4) being well-suited to the downhole environment because, in the lab, the catalyst and sample are usually heated to at least 100 Celsius anyway and, downhole, elevated temperatures are already present; and 5) emitting its own light for the analysis so it is not necessary to provide a downhole light source.

Embodiments of the present disclosure include an optical analysis tool that may be utilized to perform analysis of fluid samples in a downhole environment. In various embodiments, the tool includes one or more catalysts that react with oxygen and an analyte to emit light. The emitted light may be detected, for example by a single light detector or by a spectrometer, and the spectra may be evaluated to determine or more properties of the fluid sample. In various embodiments, the catalysts may be particularly selected to react selectively with certain analytes, thereby enabling detection of particular analytes with reduced interference from similar compounds. For a single catalyst, the spectra of emitted light may change somewhat with analyte, which provides an additional means for discriminating chemically similar compounds from one another. Furthermore, in embodiments, the one or more catalysts may be heated, for example via a power supply. The catalysts may be continuously heated, or maintained at a certain temperature, or intermittently heated. In various embodiments, the reaction rate between the catalysts and analyte may be accelerated through temperature increases to increase the cataluminescence light generated. Typically, chemical reaction rates double for every 10 degrees Celsius increase in temperature. Because optical detectors such as photodiodes are known to have increased dark currents at elevated downhole temperatures, the catalyst temperature may be cycled up and down using a resistive or other heater to produce more or less light in a cyclic manner. The presence of a modulated signal from the photodiode, which follows the modulated temperature, provides confirmation that the analyte signal is real and is not simply a dark current increase with temperature. Accordingly, embodiments of the present disclosure describe systems and methods for utilizing CTL in a downhole environment to conduct fluid analysis.

FIG. 1 is a schematic side view of an embodiment of a wellbore system 100 that includes a tool 102 (which may be part of a tool string) being lowered into a wellbore 104 formed in a formation 106 from a surface location 108. The illustrated wellbore system 100 may be referred to as a wireline system because the tool 102 is conveyed on a cable 110, such as an electric wireline although this analysis system could also be deployed on a drill string for measurement while drilling. In various embodiments, the electric wireline may transmit electric signals and/or energy from the surface location 108 into the wellbore, for example to provide operational power for the tool 102 and/or to transmit data, such as data obtained from sensors arranged on the tool 102. In various embodiments, the tool 102 may be utilized to perform downhole logging operations, and may be an imaging tool, a resistivity tool, a nuclear tool, or any other logging tool that may be used in a downhole environment. However, for the purposes of the present disclosure, the tool 102 will be described as an optical fluid analysis tool that has a probe that can be extended to contact the well bore wall for extracting fluid from the formation and that can use optical measurements to determine chemical composition of that withdrawn fluid.

As described above, in various embodiments the tool 102 may be part of a tool string 112, which may include various components utilized for wellbore operations. For example, the tool string 112 may include various other tools 114A-114C that may include sensors, measurement devices, communication devices, and the like, which will not all be described for clarity. In various embodiments, the tool string 112 may include one or more tools to enable at least one of a logging operation, a perforating operation, or a well intervention. For example, nuclear logging tools, fluid sampling tools, core sampling devices, and the like may be utilized in logging operations. Perforating operations may include ballistic devices being lowered into the wellbore to perforate casing or the formation. Furthermore, well interventions may include operations related to analyzing one or more features of the wellbore and proceeding with performing one or more tasks in response to those features, such as a data acquisition process, a cutting process, a cleaning process, and the like. Accordingly, in various embodiments, the tool string 112 may refer to tools that are lowered into the wellbore. Additionally, passive devices such as centralizers or stabilizers, tractors to facilitate movement of the tool string 112 and the like may also be incorporated into the tool string 112.

In various embodiments, different power and/or data conducting tools may be utilized by embodiments of the present disclosure in order to send and receive signals and/or electrical power. As will be described below, in various embodiments sensors may be incorporated into various components of the tool string 112 and may communicate with the surface or other tool string components, for example via communication through the cable 110, mud pulse telemetry, wireless communications, wired drill pipe, and the like. Furthermore, it should be appreciated that while various embodiments include a wireline system, in other embodiments rigid drill pipe, coiled tubing, or any other downhole exploration and production methods may be utilized with embodiments of the present disclosure.

The wellbore system 100 includes a wellhead assembly 116 shown at an opening of the wellbore 104 to provide pressure control of the wellbore and allow for passage of equipment into the wellbore 104, such as the cable 110 and the tool string 112. In this example, the cable 110 is a wireline being spooled from a service truck 118. The illustrated cable 110 extends down to the end of the tool string 112. In operation, the cable 110 may be provided with slack as the tool string 112 is lowered into the wellbore 104, for example to a predetermined depth. In various embodiments, a fluid may be delivered into the wellbore 104 to drive movement of the tool string 112, for example where gravity may not be sufficient, such as in a deviated wellbore. For example, a fluid pumping system (not illustrated) at the surface may pump a fluid from a source into the wellbore 104 via a supply line or conduit. To control the rate of travel of the downhole assembly, tension on the wireline 110 is controlled at a winch on the surface, which may be part of the service tuck 118. Thus, the combination of the fluid flow rate and the tension on the wireline may contribute to the travel rate or rate of penetration of the tool string 112 into the wellbore 104. The cable 110 may be an armored cable that includes conductors for supplying electrical energy (power) to downhole devices and communication links for providing two-way communication between the downhole tool and surface devices. Moreover, in various embodiments, tools such as tractors and the like may further be disposed along the tool string 112 to facilitate movement of the tool string 112 into the wellbore 104. Thereafter, in various embodiments, the tool string 112 may be retrieved from the wellbore 14 by reeling the cable 110 upwards via the service truck 118. In this manner, logging operations may be performed as the tool string 112 is brought to the surface 108.

In the embodiment illustrated in FIG. 1, the tool 102 may be an optical fluid analysis tool. For example, typical fluid analysis tools may use a light source directed toward a fluid medium. The light may interact with the fluid differently by absorption, fluorescence, or refractive-index-mismatch reflections at a window-fluid interface, depending on the composition of the fluid medium, and different output wavelengths may be detected, for example, by a spectrometer. An analysis of the spectra from various fluid media may enable identification of the composition of the fluid medium. As will be described below, prior methods utilized a light source that was tripped into the wellbore and also used an external power source to provide power to the light source. This steady state light source would often be exposed to high temperatures, which, for solid state light sources such as LEDs or laser diodes, would cause a dimming of their light output and reduce the output results. Tungsten light sources have filaments that operate at 3000 Kelvin, which is far above borehole temperatures, so they do not dim downhole. However, they consume much more electrical power than LEDs or laser diodes and their light output is spread over a broad spectrum rather than being concentrated in a few narrow wavelength bands of most interest such as the oil and water absorption bands. In various embodiments, techniques may be deployed for cooling a solid state light source, which adds complexity and weight to the tool. Furthermore, the wavelengths of light emitting diodes and laser diodes shift to the red with increasing temperature. Moreover, it may be difficult to find suitable solid state light sources whose light is at the wavelengths best absorbed by particular chemicals. Furthermore, in certain embodiments, significant quantities of fluid are utilized in the measurements. Accordingly, embodiments of the present disclosure are directed toward an optical fluid analysis tool utilizing an on-board, chemically-generated light source that provides increased sensitivity to different chemical compositions. Furthermore, in various embodiments, the chemically generated light source may provide greater specificity for particular chemicals and further have improved signal intensity when exposed to heat. As a result, embodiments of the present disclosure overcome various problems experienced with previous methods while also providing greater sensitivity to the analysis and simpler tooling.

Figure 2:
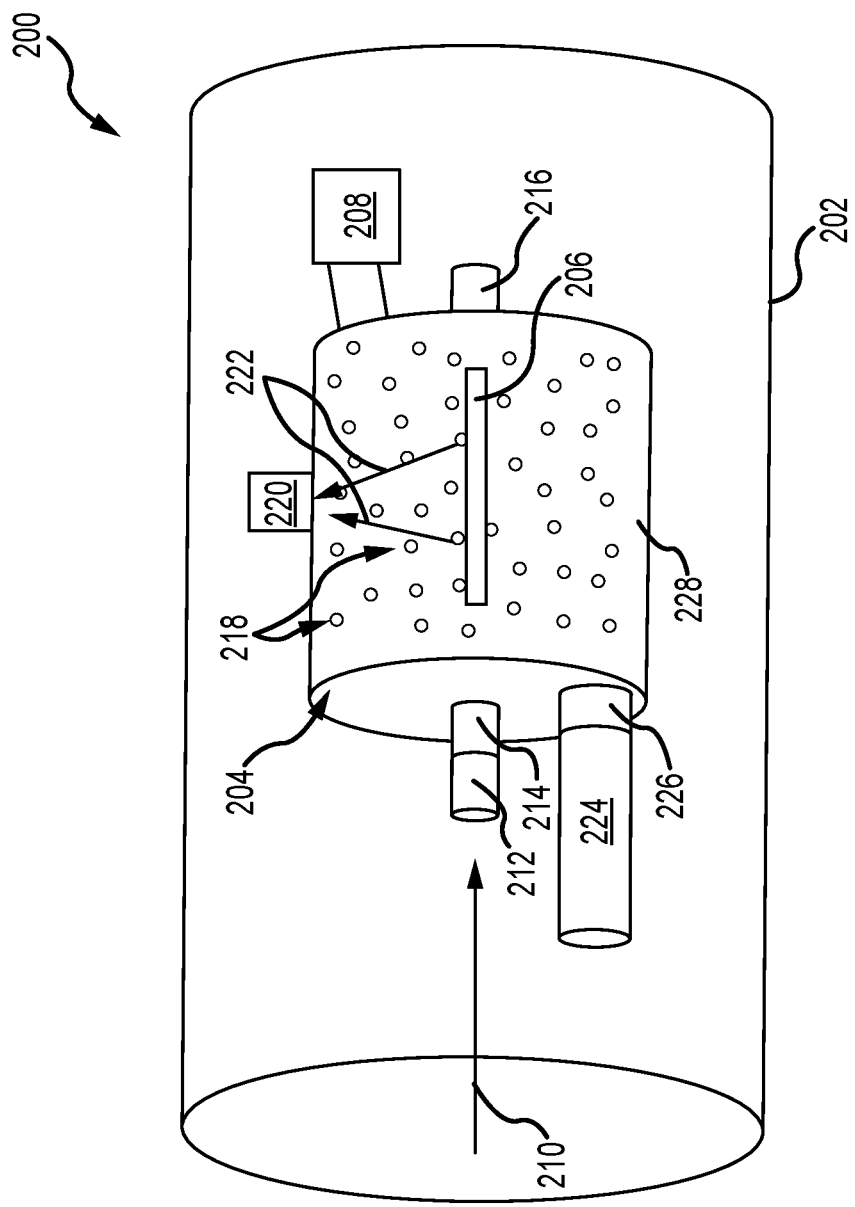
FIG. 2 is a schematic diagram of an embodiment of an optical analysis tool, in accordance with embodiments of the present disclosure.

FIG. 2 is a schematic diagram of an embodiment of an optical fluid analysis tool 200 that utilizes a cataluminescence as a light source in a downhole environment. The illustrated tool includes a housing 202 that receives a carrier 204 containing one or more catalysts 206. Such catalysts may coat the inside of carrier 204 or they may be concentrated in one region within 204 for more rapid temperature cycling using a localized heating strip rather than having to heat all of carrier 204. In the latter case, the inside of 204 may be coated with a mirror finish to collect more of the cataluminescence light emitted in various directions for detection by photodector 220, which penetrates the carrier 204. The illustrated carrier 204 is depicted as generally cylindrically shaped, however, it should be appreciated that in other embodiments the carrier 204 can be any reasonable shape. In various embodiments, the catalyst 206 enables the cataluminescence reaction to occur in the presence of an analyte and oxygen. As a result, the reaction emits light that may be specific or correlated to particular analytes and particular catalysts. This emitted light is independent of an external light source, unlike prior methods of optical fluid analysis. Accordingly, in embodiments, various catalysts 206 may be used to detect various different types of analytes.

It should be appreciated that, in various embodiments, the one or more catalysts 206 may be particularly selected to react with or otherwise identify certain analytes. As described above, the catalyst 206 may have high sensitivity to certain chemicals or compounds, as a result, selecting these catalysts 206 may enable detection of particular chemicals or compounds within a fluid sample introduced into housing 202. A non-limiting list for potential catalyst 206 includes $BaCO_3$, $CdC_{12}$, $CdO$, $CdS$, $Co_3O_4$, $Fe_2O_3$, $Fe_3O_4$, $In_2O_3$, $La(OH)_3$, $La_2O_3$, $MgO$, $NaYF_4{:}Er$, $SrCO_3$, $TiO_2$, $V_2Ti_4O_{13}$, $Y_2O_3$, $ZnO$, $Zn_3SnLa_2O_8$, $ZrO_2$, various metal-organic frameworks, composites thereof, and the like.

In embodiments, the housing 202 is a pressure housing configured to withstand typical wellbore temperatures and pressure. As will be described below, in various embodiments, increased temperatures may be beneficial for operation of the tool 200. Accordingly, special insulating materials or heat exchangers may not be needed with embodiments of the present disclosure, thereby reducing costs and weight of the tool 200. The housing 202 may be formed from a variety of different materials, such as metals. Moreover, in the embodiment illustrated in FIG. 2, the tool 200 further includes a power supply 208 coupled to the carrier 204. In various embodiments, the power supply 208 provides an electrical current, for example to a heating coil within the carrier 204, that increases the temperature of the carrier 204 or a heating strip that just heats a localized region of catalyst 206 for more rapid temperature cycling. This current may be continuous or intermittent, for example pulsed or sinusoidal. Because the addition of heat may improve the chemical reaction that generates light, it may be advantageous to provide additional heat to the carrier 204, and therefore to the catalyst 206. Alternatively, heating of the catalyst 206 alone is provided by a heating strip, which allows for faster temperature rise and fall and power usage than would heating the entire carrier 204. Furthermore, in embodiments, the power supply 208 may be used to heat the catalyst 206 from a temperature below significant light emission to a temperature above significant light emission. Such an approach provides confirmation of the analyte presence due to the change in light intensity with the change in catalyst temperature, which would not occur if the photodiodes signal were simply due to a temperature-caused increase in its dark current. Modulating the catalyst temperature would also enable use of a digital filter or a lock in amplifier to improve signal to noise.

As described above, the carrier 204 forms a volume, which is filled, at least partially, with oxygen. The presence of the oxygen, analyte, and catalyst 206 enables the reaction that emits light, which can be detected by one or more detectors to determine the analyte. In the illustrated embodiment, a fluid sample 210 is injected into the carrier 204 via an inlet 212. The inlet 212 may be a controlled inlet that enables a predetermined or small amount of the fluid sample 210 to pass into the carrier 204. As will be appreciated, if the fluid sample 210 were allowed to entirely fill the carrier 204, the oxygen would be displaced, and no reaction with the catalyst 206 would occur. The flow into the carrier 204 may be controlled by a regulator 214. In various embodiments, the regulator 214 opens or closes access to a permeable membrane, such as the membrane discussed in U.S. Pat. No. 7,219,541, which is hereby incorporated by reference. Furthermore, in embodiments, the regulator 214 is an injector, such as the injector discussed in U.S. Pat. Nos. 8,955,375 and 8,145,429, both of which are hereby incorporated by reference. The injected volume is small, such as the amount of fluid contained in a 20 nanoliter scratch on a rotating plate, which collects a bit of fluid from the high pressure side and flashes it into the much larger and low pressure reaction chamber. Accordingly, small amounts of the fluid sample 210 may be introduced into the carrier, analyzed, and thereafter removed from the carrier 204 via an outlet 216. A spare oxygen tank 224 through control valve 226 may be used to flush the old sample as well as to provide make up oxygen for the oxygen that is consumed. It should be appreciated that, in various embodiments, the interior of the carrier 204 may be referred to as a reaction chamber 228 because the reaction between the catalyst 206 and an analyte 218 may take place within the volume formed by the carrier 204. However, in other embodiments, the reaction chamber 228 may correspond to the interior of the housing 202, for example, where the catalyst 206 is deposited on an exterior of the carrier 204. Furthermore, in various embodiments the inlet 212, outlet 216, and the like are described with reference to the carrier 204. However, it should be appreciated that various inlets, outlets, and the like may also be associated with the housing 202 to facilitate the introduction of the fluid sample 210. For example, the inlet 212 may extend to the housing 202.

In various embodiments, the fluid sample 210 includes an analyte 218, which as used herein describes a substance or chemical constituent that is of interest in an analytical procedure. For example, the analyte may include H2S, CO2, N2, various hydrocarbons, and the like. In operation, the analyte 218 will react with the catalyst 206 and the oxygen to generate light. Different chemical compounds may generate light at different wavelengths (e.g., colors) when exposed to one or more different catalysts 206. In various embodiments, a detector 220, such as photodetectors or spectrometer arrays, may be arranged proximate to or within the housing 202 to detect the light. For example, while the illustrated embodiment includes a photomultiplier tube, avalanche photodiode, or other photodiode, which detects the emitted light 222, in various embodiments, different detectors, such as optical fibers that are embedded within the housing 202, may be utilized. It should be appreciated that, in various embodiments, the housing 202 may be formed with a window or opening to enable detection of the light from a location external to the housing 202. The photodetection could be done with a spectrometer as well.

In various embodiments, the tool 200 further includes a spare tank 224 that may provide additional oxygen to the housing 202 through control valve 226. For example, in various embodiments, the spare tank 224 may store the oxygen under pressure and direct the oxygen into the housing 202. In certain embodiments, the housing 202 may include one or more sensors that detect an oxygen percentage in the housing 202. Upon detection of an oxygen percentage below a threshold, the spare tank 224 may release the oxygen into the housing 202. In this manner, sufficient oxygen for reactions between the analytes 218 and the catalyst 206 may be maintained within the housing 202.

Figure 3:
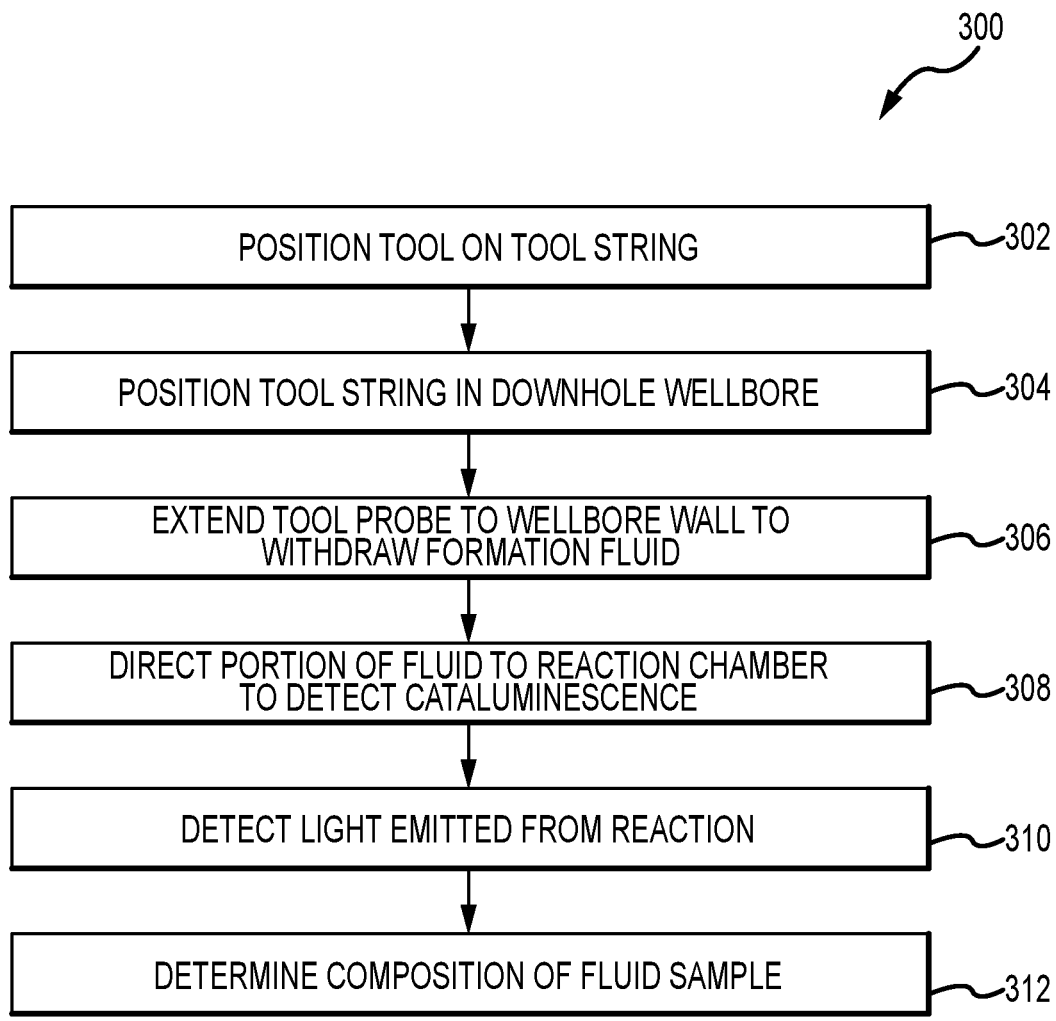
FIG. 3 is a flow chart of an embodiment of a method for performing a downhole optical analysis, in accordance with embodiments of the present disclosure.

FIG. 3 is a flow chart of an embodiment of a method 300 for determining a fluid sample composition. It should be appreciated that for this method, and all other methods described herein, that the steps may be performed in parallel or in a different order, unless otherwise explicitly stated. Furthermore, there may be more or fewer steps. In this example, a downhole tool, such as an optical analysis tool, is positioned on a tool string (block 302). For example, the tool 200 may be positioned on the tool string 112. The tool string is conveyed into a downhole wellbore (block 304). For example, the tool string 112 may be conveyed via the wireline cable 110 into the wellbore 104 formed in the downhole formation 106. Moreover, in embodiments, the tool string 112 may be part of a drilling string or other rigid tubing pipe that is positioned within the wellbore.

In various embodiments, a fluid sample flow path is provided (block 306) to enable the fluid sample to enter a body of the tool. This could be done with a rubber rimmed probe that extends from the tool to the wellbore wall where it forms a seal and, by lowering the pressure, withdraws formation fluid from the wellbore wall. For example, the inlet 212, which may include the regulator 214, may enable the sample fluid to enter into the housing 202 and/or the carrier 204. Analytes of the fluid sample react with oxygen within the housing and with a catalyst, in a cataluminescence reaction, to emit light (block 308). In various embodiments, the carrier 204 arranged within the housing 202 is coated with one or more catalysts 206, as described above. The catalysts 206 react with the analytes 218 in the fluid sample and the oxygen to generate light. As described above, in various embodiments, the light emitted through the reaction may be indicative of certain analytes and/or catalysts. The emitted light is detected (block 310), for example via silicon photodetectors or spectrometer arrays, and a composition of the fluid sample is determined (block 312). Accordingly, optical fluid analysis is performed in the downhole environment without conveying a separate light source downhole as the reaction within the tool 200 generates the light utilized in the optical analysis. In various embodiments, analysis of the fluid properties based on the optical analysis tool may be utilized to inform physical decisions at the wellbore, such as well interventions, treatments, and the like.

Figure 4:
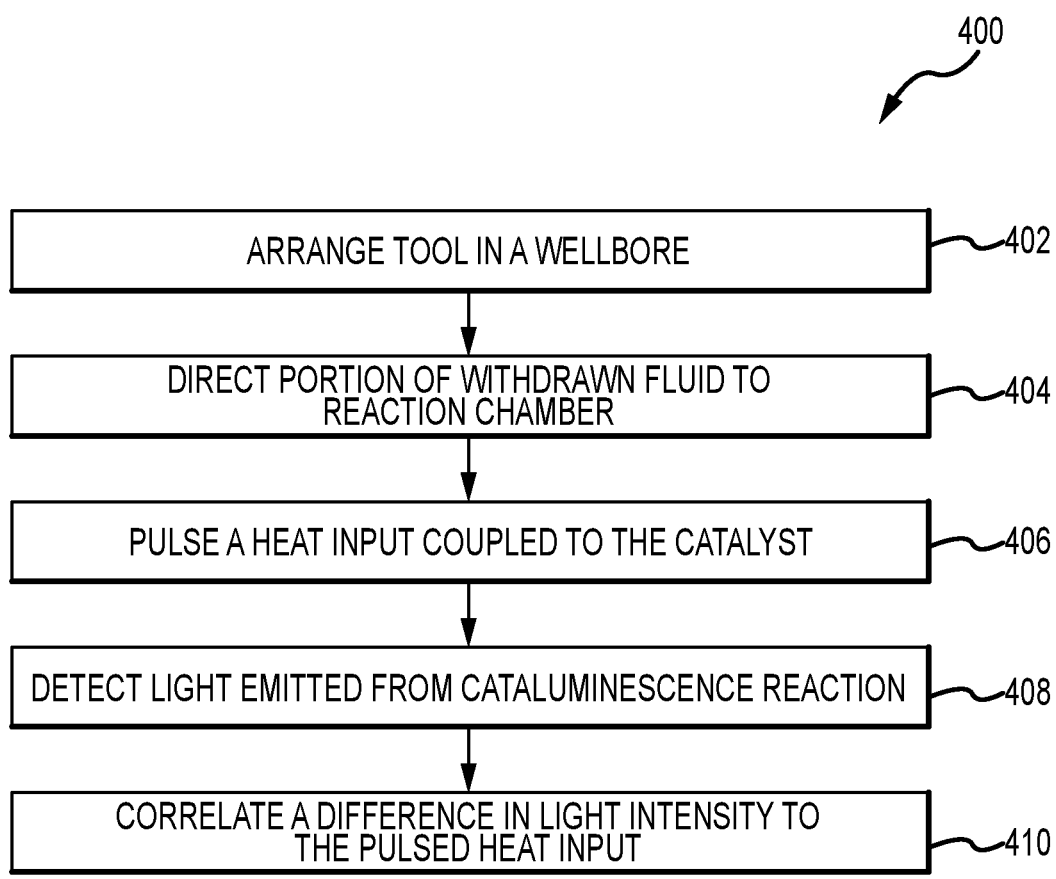
FIG. 4 is a flow chart of an embodiment of a method for performing a downhole optical analysis, in accordance with embodiments of the present disclosure.

FIG. 4 is a flow chart of a method 400 for conducting downhole optical fluid analysis. In this example, a tool is arranged within a wellbore (block 402). For example, the optical analysis tool 200 may be arranged in the wellbore 104 formed in the formation 106. In various embodiments, the tool 200 may form at least a portion of the larger tool string 112. A flow path for a fluid sample is provided into the body of the tool (block 404). For example, the fluid sample 210 may be directed into the reaction chamber 228. In various embodiments, as described above, the flow path may be controlled by the regulator 214 such that a small amount or a pre-determined amount is directed into the tool. In this example, a heat source is pulsed to transmit heat energy to a catalyst within the tool (block 406). For example, the power supply 208 may be coupled to the carrier 204 including the one or more catalysts 206. As described above, in various embodiments, increasing the heat of the catalysts 206 may improve the reaction rate with various analytes and the oxygen. Energy from the power supply 208 may be cycled or intermittently provided to the carrier 204 or directly to the catalyst 206. Moreover, in embodiments, a period of time between pulses may be predetermined to enable cooling of the catalyst 206 to a desired temperature or within a range. The light emitted from the reaction may be detected (block 408). For example, the detector 220 may be arranged proximate the housing 202 or within the housing 202 to detect the emitted light 222. In various embodiments, the emitted light 222 may be at a variety of wavelengths, which may correspond to the analytes 218 within the housing 202. Furthermore, in embodiments, the signal detected by the detector 220 may be larger when the catalyst 206 is heated, as opposed to times when the catalyst 206 is not heated. As such, in various embodiments, a difference between the light intensities may be correlated to times when the heater is activated (block 410). Correlating the heating times with the light intensities may confirm the presence of the analyte 218, as opposed to detecting an increased light intensity due to temperature-caused increases in dark currents of the photodetectors. Accordingly, in embodiments, the pulsed heat source may be utilized to increase light intensities corresponding to detections of analytes and also verify analyte presence over potential noise. In various embodiments, analysis of the fluid properties based on the optical analysis tool may be utilized to inform physical decisions at the wellbore, such as well interventions, treatments, and the like.

Figure 5:
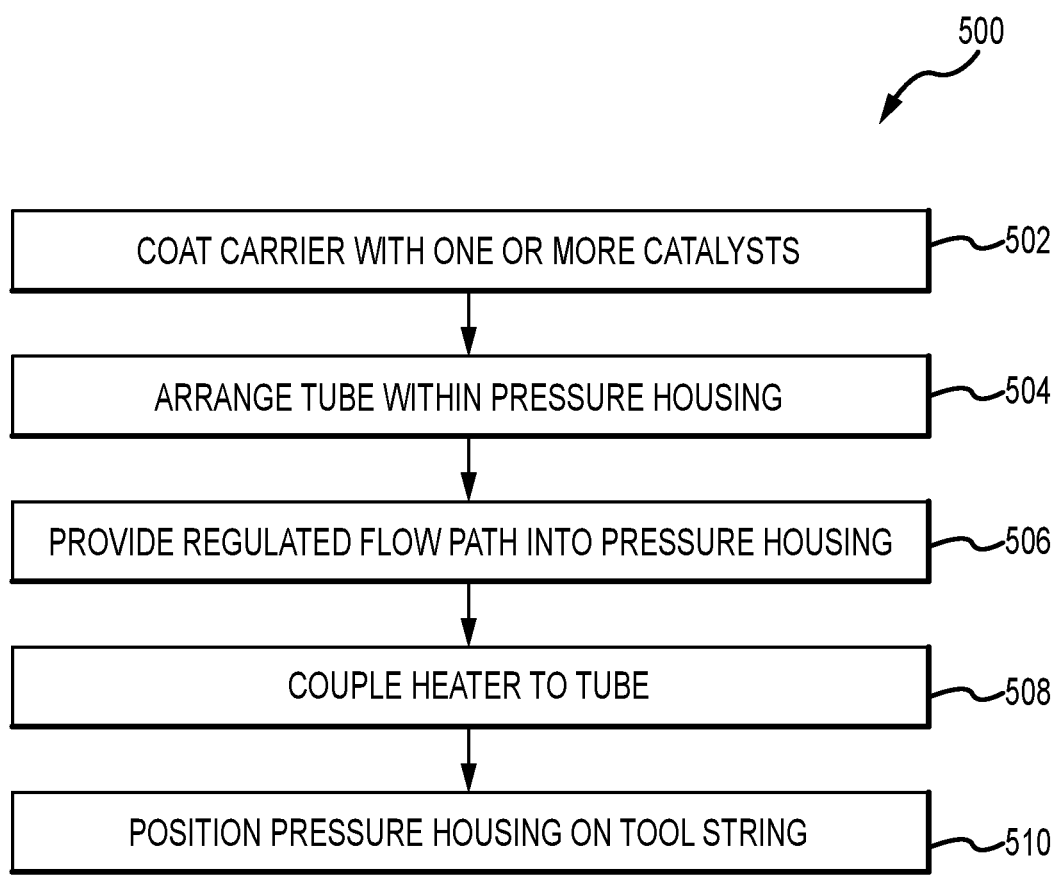
FIG. 5 is a flow chart of an embodiment of a method for forming an optical analysis tool, in accordance with embodiments of the present disclosure.

FIG. 5 is a flow chart of an embodiment of a method 500 for forming a downhole optical analysis tool. In this example, a carrier is coated with one or more catalysts (block 502). As described above, the catalysts 206 may be particularly selected to react with one or more analytes 218. In various embodiments, certain analytes 218 of interest may be selected and corresponding catalysts 206 may be selected accordingly. In various embodiments, the carrier is arranged within a pressure housing (block 504). For example, because the tool 200 will be utilized in a downhole environment, the pressure housing 202 may be utilized in order to withstand wellbore temperatures and pressures. Furthermore, in various embodiments, the pressure housing 202 may further be used to constrain oxygen and the analytes 218 from the surrounding environment for analysis. A regulated flow path into the pressure housing is provided (block 506). For example, the regulated flow path may restrict a quantity of a fluid sample into the pressure housing 202. As a result, the fluid sample 210 will not totally displace the oxygen or use up the oxygen in the pressure housing 202, which would prevent the reaction between the analyte 218 and the catalyst 206 from taking place. In embodiments, a power supply is coupled to the carrier (block 508) or to the catalyst directly. The power supply 208 may be pulsed to provide intermediate heat energy to the carrier 204, which is transferred to the catalyst 206 or it could directly heat the catalyst 206. As described above, in embodiments, reactions between the catalyst 206 and the analyte 218 may be improved by heating the catalyst 206. Moreover, in embodiments, the heat energy may be intermittently pulsed to the carrier 204 to provide signatures indicative of the analytes 218 during analysis. That is, the signal during the heating period will likely be larger than the signal when the carrier is not heated, and as a result, noise may be reduced by evaluating signals during the unheated period. In various embodiments, the tool is positioned on a tool string (block 510) which may be used in a downhole environment. Accordingly, in various embodiments, the optical analysis tool may be formed that enables use in a downhole environment without providing a separate light source for optical fluid analysis.

In various embodiments, various instrumentation units and data collection units may be utilized that may include a digital and/or an analog system. For example, the tool 102 may include digital and/or analog systems. Furthermore, various surface and wellbore components not illustrated for clarity may also use a variety of digital and/or analog systems. The system may have components such as a processor, storage media, memory, input, output, communications link (wired, wireless, optical or other), user interfaces (e.g., a display or printer), software programs, signal processors (digital or analog) and other such components (such as resistors, capacitors, inductors and others) to provide for operation and analyses of the systems and methods disclosed herein. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery, magnet, electromagnet, sensor, electrode, transmitter, receiver, transceiver, antenna, controller, optical unit, electrical unit or electromechanical unit) may be included in support of the various aspects discussed herein or in support of other functions beyond this disclosure.

The foregoing disclosure and description of the disclosed embodiments is illustrative and explanatory of the embodiments of the invention. Various changes in the details of the illustrated embodiments can be made within the scope of the appended claims without departing from the true spirit of the disclosure. The embodiments of the present disclosure should only be limited by the following claims and their legal equivalents.

The invention claimed is:

1. A system for performing a downhole optical analysis, the system comprising:
   a housing positioned in a wellbore extending into a formation;
   a carrier arranged within the housing, the carrier being coupled to a power supply;

a catalyst coating at least a portion of the carrier;

a regulated inlet providing a fluid pathway into a reaction chamber that includes at least a portion of the catalyst; and a detector arranged relative to the reaction chamber to detect a signal emitted via an interaction between the catalyst and a fluid sample introduced into the housing.

2. The system of claim 1, wherein the power supply intermittently provides an electrical signal to the carrier that heats the catalyst.

3. The system of claim 1, wherein the detector is arranged within the reaction chamber.

4. The system of claim 1, wherein the detector is arranged external to the reaction chamber, the system further comprising:

a view port arranged in a wall of the carrier, the detector being aligned with the view port, and the reaction chamber being at least partially defined by the carrier.

5. The system of claim 1, wherein the detector is a light detector and the signal is light emitted from a reaction between the catalyst, oxygen within the reaction chamber, and an analyte of the fluid sample.

\* \* \* \* \*